(12) United States Patent
Popa

(10) Patent No.: US 11,338,221 B2
(45) Date of Patent: *May 24, 2022

(54) HEAT EXCHANGER

(71) Applicant: STAMICARBON B.V., Sittard (NL)

(72) Inventor: Dorin Popa, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/114,317

(22) Filed: Dec. 7, 2020

(65) Prior Publication Data

US 2021/0187412 A1 Jun. 24, 2021

Related U.S. Application Data

(63) Continuation of application No. 16/469,129, filed as application No. PCT/NL2018/050711 on Oct. 26, 2018, now Pat. No. 10,857,480.

(30) Foreign Application Priority Data

Oct. 27, 2017 (EP) .................................. 17198990

(51) Int. Cl.
*B01D 5/00* (2006.01)
*B01J 10/00* (2006.01)
(Continued)

(52) U.S. Cl.
CPC ......... *B01D 5/0075* (2013.01); *B01D 5/0009* (2013.01); *B01D 5/0081* (2013.01);
(Continued)

(58) Field of Classification Search
CPC ...... C07C 273/04; C07C 273/14; B01J 10/00; B01J 19/02; F28D 7/06; F28D 2021/0022; F28D 2021/0063; B01D 5/00075; B01D 5/0009; B01D 5/0081; B01D 5/0084; B01D 5/0087; F28F 9/0202; F28F 9/0239; F28F 9/0246
See application file for complete search history.

(56) References Cited

U.S. PATENT DOCUMENTS 2,256,882 A * 9/1941 Sebald ...................... F28D 7/06
                                                          165/72
3,254,705 A * 6/1966 Worthen et al. ........ F22B 1/123
                                                          165/71
(Continued)

FOREIGN PATENT DOCUMENTS

CN          204924007 U     12/2015
CN          105699201        6/2016
(Continued)

OTHER PUBLICATIONS

International Search Report and Written Opinion for PCT/NL2018/050711, dated Feb. 21, 2019, 8 pages.
(Continued)

*Primary Examiner* — Lessanework Seifu
(74) *Attorney, Agent, or Firm* — Leason Ellis LLP

(57) ABSTRACT

Disclosed is a shell-and-tube heat exchanger type with a tube bundle and has a redistribution chamber connected to tubes of the tube bundle and to a duct. The duct extends between the redistribution chamber and the shell.

13 Claims, 3 Drawing Sheets

(51) Int. Cl.
*F28D 9/02* (2006.01)
*C07C 273/04* (2006.01)
*C07C 273/14* (2006.01)
*F28D 7/06* (2006.01)
*F28F 9/02* (2006.01)
*F28D 21/00* (2006.01)

(52) U.S. Cl.
CPC ......... *B01D 5/0087* (2013.01); *B01D 5/0093* (2013.01); *B01J 10/00* (2013.01); *C07C 273/04* (2013.01); *C07C 273/14* (2013.01); *F28D 7/06* (2013.01); *F28F 9/0202* (2013.01); *F28F 9/0246* (2013.01); *F28D 2021/0022* (2013.01); *F28D 2021/0063* (2013.01); *F28F 2009/0287* (2013.01)

(56) References Cited

U.S. PATENT DOCUMENTS

| | | |
|---|---|---|
| 4,082,797 A | 4/1978 | Zardi et al. |
| 4,899,813 A | 2/1990 | Menicatti et al. |
| 5,767,313 A | 6/1998 | Jonckers |
| 6,093,850 A | 7/2000 | Kojima et al. |
| 6,518,457 B1 | 2/2003 | Sakata et al. |
| 2001/0031893 A1 | 10/2001 | Pagani et al. |
| 2004/0116743 A1 | 6/2004 | Mennen |
| 2008/0085229 A1 | 4/2008 | Pennino |
| 2015/0086440 A1 | 3/2015 | Scheerder |
| 2015/0119603 A1 | 4/2015 | Van Den Tillaart et al. |
| 2016/0075642 A1 | 3/2016 | Takahashi et al. |

FOREIGN PATENT DOCUMENTS

| | | |
|---|---|---|
| EP | 0 464 307 | 1/1992 |
| GE | P201706706 | 7/2017 |
| IN | 1008DEN2015 A | 6/2015 |
| WO | WO-2017/014632 | 1/2017 |

OTHER PUBLICATIONS

Stamicarbon, "A lower cost design for urea", Nitrogen No. 222, July-Aug. 1996, pp. 29-31.

* cited by examiner

HEAT EXCHANGER

CROSS-REFERENCE TO RELATED APPLICATIONS

This application is a continuation of U.S. Ser. No. 16/469,129 filed 12 Jun. 2019, and now U.S. Pat. No. 10,857,480 issued 8 Dec. 2020, which is the U.S. national phase of PCT application PCT/NL2018/050711 filed 26 Oct. 2018, which claims benefit of European patent application No. 17198990.8 filed 27 Oct. 2017. The contents of the above patent applications are incorporated by reference herein in their entirety.

INTRODUCTION

The invention pertains to a high pressure carbamate condenser. The condenser comprises a shell-and-tube heat exchanger which comprises a tube bundle mounted in a shell. The high pressure carbamate condenser can in particular be used for condensing carbamate in urea production plants of the stripping type. In some embodiments, corrosive solutions comprising carbamate are present in operation at both the shell side and the tube side, in particular both inside at least some tubes of the tube bundle and in the space between the tubes.

A commonly used type of carbamate condenser is the pool condenser described in "A lower cost design for urea", Nitrogen no. 222, July-August 1996, page 29-31. Such a pool condenser comprises a tube sheet. Tube sheets are more generally a typical part of high pressure carbamate condensers of the shell-and-tube heat exchanger type. The tube sheet is typically a planar metal plate delimiting the shell space in the condenser from a header. The tube sheet furthermore seals off one end of the typically cylindrical shell. The tube sheet is provided with numerous bore holes. The tubes are inserted through the bore holes or are joined to the tube sheet aligned with the holes, such that fluid can flow between a header and the tubes. The tube bundle often has a very large number of tubes, e.g. more than 100 tubes or even more than 1000 tubes. The header is used for distributing fluid from an inlet to a plurality of tubes, or for collecting fluid from a plurality of tubes to an outlet.

In known carbamate condensers, the tube sheet generally needs to be able to withstand high pressure. Furthermore, preventing corrosion is a challenge because carbamate is highly corrosive, especially at the high temperatures of high pressure carbamate condensation. To achieve high mechanical strength and high corrosion resistance, known tube sheets are frequently made from carbon steel lined with a layer of highly corrosion resistant steel such as duplex stainless steel alloys on the side (or sides) exposed to corrosive medium. This increases construction costs, for example because of the difficult welding of the tubes to the tube sheet.

A known tube sheet for a kettle type carbamate condenser in a urea plant is illustrated in EP 0464307 and in U.S. Pat. No. 4,082,797.

The construction of the tube sheet is generally challenging and expensive. The present invention generally addresses disadvantages of known high pressure carbamate condensers with tube sheets, such as the high construction costs associated with the tube sheet.

SUMMARY

The present disclosure relates in a first aspect to a shell-and-tube heat exchanger which comprises a vessel which comprises a shell and at least one tube bundle, wherein the shell encloses a vessel space, wherein the tube bundle comprises tubes having ends, and wherein a shell space is provided between the tubes and the shell, wherein the heat exchanger further comprises a redistribution chamber located in said vessel space, wherein said redistribution chamber comprises a wall for separating a first fluid in the shell space from a second fluid inside the redistribution chamber, wherein a plurality of said tubes are connected to a single redistribution chamber such that said second fluid can flow between said tubes and said redistribution chamber, wherein the condenser further comprises a duct extending from an opening for the second fluid in said shell through said vessel space to said redistribution chamber, such that the second fluid can flow between a tube end and said opening for the second fluid in said shell through said redistribution chamber and said duct.

The invention also pertains to a urea production plant comprising a high pressure urea synthesis section comprising a reactor, a stripper and a high pressure carbamate condenser, wherein the high pressure carbamate condenser is as described, and wherein optionally the reactor and the high pressure carbamate condenser are combined in a single vessel which vessel has a liquid outlet connected to the stripper.

The invention further pertains to a urea production process wherein urea is formed in a reactor to give urea synthesis solution, at least a part of said urea synthesis solution is stripped in a stripper to give stripped urea solution, and wherein gas from the stripper is condensed in a high pressure carbamate condenser, wherein the process is carried out in a plant as described and/or wherein the high pressure carbamate condenser is as described.

More generally, the invention also pertains to a shell-and-tube heat exchanger comprising such a vessel and comprising such a shell, tube bundle, redistribution chamber and duct. The shell-and-tube heat exchanger is e.g. configured for condensation of compounds other than carbamate, and/or for operation at pressures below 100 bar, and/or for heat exchange processes other than condensation. The heat exchanger can be used in urea production and in other plants and processes.

DETAILED DESCRIPTION

Figure 1:
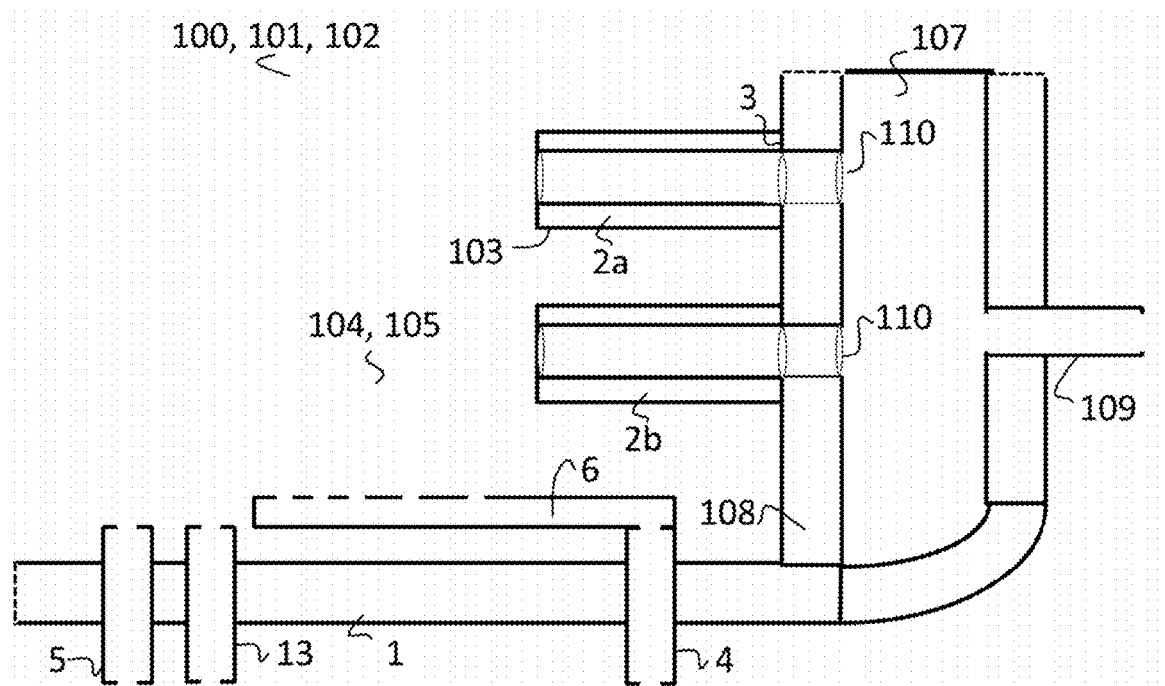
FIG. 1 illustrates a reference carbamate condenser with a tube sheet.

In this application, for process streams (i.e. not for steam lines), high pressure (HP) is above 100 bar, for instance 120 to 300 bar, typically 150 to 200 bar. Medium pressure (MP) is for example 10 to 70 bar (including intermediate pressure of 30 to 70 bar), in particular 15 to 25 bar, and low pressure (LP) is for example 0 to 10 bar, in particular 1 to 8 bar or 2 to 5 bar. As used herein, "carbamate" refers to ammonium carbamate.

The high pressure carbamate condenser is preferably a submerged condenser, as opposed to a falling film condenser. In operation of a submerged condenser, the condensation is carried out in a space with liquid as the continuous phase and with the gas to be condensed dispersed in the liquid. A liquid level is hence present in the condensation space. For example, the tubes are covered by the condensed liquid in operation (on the inside or on the outside of tubes), and preferably the tubes are submerged in the condensed liquid. The submerged condenser comprising a shell-and-tube heat exchanger is configured for condensation inside the tubes or in the shell space. Suitably, the condensation is carried out in the shell space. The shell space is the empty space to which the outer surface of the tubes is exposed. The shell space is confined by the shell. Condensation in the shell space is one option for providing a relatively simple construction wherein the condensate has sufficient residence time in the condenser. This allows advantageously for a part of the urea to be formed already in the condenser. A longer residence time can also be provided in case of condensation in the tubes by using more tubes and/or tubes with a larger diameter.

The condenser is e.g. a high pressure carbamate condenser configured as submerged condenser with condensation carried out in the shell space, for example based on the pool condenser design, but modified to have one or more such said redistribution chambers and ducts. An example pool condenser design is illustrated in Nitrogen No. 222, July-August 1996, pages 29-31. Preferably, cooling fluid is provided in the tubes. In the present invention, the cooling fluid is e.g. a process stream, such as a solution comprising urea and carbamate, which solution is heated when passing through the tubes, optionally water (process condensate) is in addition used as cooling fluid.

The high pressure carbamate condenser has for instance a vertical configuration, with (the straight part of) the tubes in vertical arrangement with respect to gravity, when installed in the urea plant. Generally, the vertical carbamate condenser is configured for condensation in the shell space or in the tubes, preferably in the shell space. The condenser has e.g. a U-shaped or straight tube bundle, preferably a U-shaped tube bundle. For instance a vertical carbamate condenser that is of the type described in U.S. Pat. No. 6,518,457 and/or which has a tube bundle with tube ends at the bottom can be modified with redistribution chambers and ducts according to the present invention. Furthermore a vertical condenser with a tube bundle with tube ends at the top can be provided with redistribution chambers and ducts according to the invention, these are e.g. placed at the top of the condenser.

The high pressure carbamate condenser preferably has a horizontal configuration, with (the straight part of) the tubes in horizontal arrangement with respect to gravity, when installed in the urea plant. For example, the high pressure carbamate condenser with horizontal orientation can be configured for condensation in the tubes and for receiving cooling fluid in the shell space. For instance a kettle type carbamate condenser, e.g. as described in EP 0464307 or U.S. Pat. No. 4,899,813, can be modified with a redistribution chamber and duct as described herein.

In an embodiment the condenser is configured as a horizontal submerged condenser. This advantageously allows for lower height of the plant. In a preferred embodiment, the condenser is configured as a horizontal submerged condenser operated with the condensation on the shell side (i.e. in the shell space). This provides the further advantage that the condenser volume can be easily designed for a longer residence time of the condensate. This may also be used to create a pool reactor. The condensation on the shell side also leads to having the high pressure medium on the shell side which makes the condenser easier to manufacture and in particular allows for a simpler design of the redistribution chamber.

Hence, in a preferred embodiment, the vessel comprises a gas inlet to the shell space, for gas to be condensed. The gas inlet comprises an opening in the shell. The gas inlet allows for operation with condensation in the shell space and cooling fluid(s) in the tubes. The vessel furthermore comprises an outlet for liquid from the shell space, such as for a carbamate-containing liquid stream. The outlet comprises an opening in the shell. The vessel preferably comprises a gas distributor connected to the gas inlet. The gas distributor preferably comprises a plurality of passageways for gas from the gas inlet into the shell space. The gas distributor can be used for distributing gas to be condensed over and into the shell space, in particular into the liquid in operation. The gas distributor is preferably arranged below the liquid level in operation. The gas distributor for instance comprises a sparger with one or more tubes extending in the length of the vessel, said tube provides with arms extending in the width of the vessel at both sides of said tubes, wherein the arms have numerous openings for gas (e.g. more than 50 openings per arm) at the upper side of the arms. Gas to be condensed is e.g. a mixture comprising $CO_2$ and $NH_3$ from a high pressure stripper. The vessel furthermore preferably comprises a liquid inlet to the shell space, for introducing into the shell space a liquid stream comprising ammonia and/or carbamate recycle stream. In an example embodiment, a carbamate recycle stream, e.g. from a medium pressure section of a urea plant, is introduced into the shell space through an opening in the shell at the top of the shell. This can provide for improved mixing because the carbamate recycle liquid has a higher density than the condensing mixture in the shell space. The opening in the shell for carbamate recycle is preferably in length direction spaced less than 1 m from a redistribution chamber. This provides for good mixing of fluids in the shell space near the redistribution chamber.

The carbamate condenser has e.g. a horizontal or vertical arrangement. In case of a horizontal carbamate condenser with a gas distributor, the gas distributor extends horizontal and in parallel with (the straight parts of) the tubes, so as to introduce gas to be condensed in the shell space at various outlets of the gas distributor which are spaced apart in horizontal direction. In this embodiment, the length direction is also horizontal. The tubes are preferably U-shaped.

The condenser preferably comprises a liquid distributor for distributing liquid into the shell space at a plurality of openings. These openings are preferably spaced apart in the length direction of the condenser. The liquid distributer is e.g. connected to an ammonia supply member, such as with a liquid flow connection to a compressor for ammonia feed. Typically the liquid distributor (e.g. ammonia distributor) is connected to an opening in the shell, and is in operation for instance submerged in liquid present in the shell space.

A tube bundle generally comprises a plurality of tubes, wherein the tubes comprise or consist of straight tube parts. Typically the straight parts of the tubes are arranged in parallel and are spaced apart from each other. As used in this application, if condensation is carried out in the shell, the tubes of a single tube bundle comprise the same cooling fluid. Accordingly, a redistribution chamber is preferably connected to tubes of a single tube bundle. In a further embodiment two or more cooling fluids are used in the tubes (with separate supply members), and the condenser contains a plurality of tube bundles. The tube bundles can be combined in a combined tube bundle. The straight parts of all tubes in a combined tube bundle are preferably parallel to each other.

In order to have sufficient heat exchange surface, the high pressure carbamate condenser has one or more tube bundles with for instance at least 300 tubes in the bundles in total, typically 1000 to 4000, such as 1500 to 3000 tubes in total, with e.g. at least 100 tubes in each tube bundle. Tubes have for instance constant internal diameter over their length. Preferably, each redistribution chamber is connected to only inlet ends or only outlet ends of a single tube bundle.

In some embodiments, the tube bundle comprises straight tubes with tube ends at opposed sides of the tube bundle in the length direction. Redistribution chambers can be provided at each end of the tube bundle. In principle, also a tube sheet can be used at one end and a redistribution chamber at an opposed end. The tube bundle can be located at any position in the length of the vessel, e.g. at an end or in the center of the vessel. The straight part of the tubes have for instance a length of 20-90% of the length of the vessel, e.g. preferably at least 30%, at least 40%, at least 50%, or at least 60%, and/or e.g. up to 90%, up to 80%, or up to 70% of the length of the vessel. In some embodiments, the straight parts of the tubes have a length of 60 to 90% of the length of the vessel, and preferably the condensate obtained by condensation in the condenser is supplied to a high pressure reactor. In some embodiment, the straight parts of the tubes have a length of 20 to 60% of the length of the vessel, and preferably the condensate obtained by condensation in the condenser is supplied to a high pressure stripper. For instance the condensate is supplied directly to the stripper such that the high pressure stripper receives condensate having the same composition as at the liquid at the outlet of the condenser. In a urea plant according to such embodiment, the reactor and condenser are combined in a single vessel.

In some embodiments, redistribution chambers are provided at both ends of the tubes (preferably of a straight tube bundle) and the redistribution chamber(s) are spaced apart from the vessel by a distance, in the length direction, of at least 1%, at least 5%, at least 10%, or at least 20% at the length of the vessel, at one or both ends of the tube bundle. A larger spacing between the redistribution chamber and vessel, at one or both ends of the tube bundle, gives a relatively larger shell space for condensate and may contribute to a larger residence time of condensate in the shell space. This may allow for urea formation to occur and e.g. for operation as pool reactor. The condensed carbamate is typically sent to a urea reactor and is in some embodiments sent directly to the stripper in operation. Especially for larger tube lengths (based on the straight tube part), such as above 5 m, above 10 m, above 20 m, or above 30 m, the manufacturing of straight tubes can be simpler than for U-shaped tubes.

In further embodiments, the tube bundle is a bundle of U-shaped tubes, wherein each tube comprises a bend and two legs, the legs being straight tube parts. The carbamate condenser optionally comprises a reactor part between the bend of the U-shaped tube bundle and the shell (opposite of the tube legs), for example but not exclusively in case of a pool reactor. An example pool reactor is described in U.S. Pat. No. 5,767,313. The straight parts of the tubes of the U-shaped tube bundle are arranged in the length direction of the shell. In some embodiments, the shell comprises an essentially cylindrical middle part, having a diameter and a length, and with cap parts at both ends. In case of a U-shaped tube bundle, for instance a substantially hemispherical cap (optionally with a manhole) is joined to the end of the middle part that is close to the bend of the tube-bundle of the tube bundle as well as at the other end of the middle part. In the prior art, e.g. as in U.S. Pat. No. 5,767,313, a tube sheet is provided at end away from the bend of the U-shaped tube-bundle, to connect the tube ends with feed and drain lines through a header.

The invention is broadly based on the judicious insight to place a redistribution chamber inside the shell and to connect tubes of the tube bundle to the redistribution chamber, and to provide a duct connecting the redistribution chamber with a feed or drain line through an opening in the shell. The duct is arranged inside the shell and allows the redistribution chamber to be spaced apart from the shell. The duct is in operation at one side in contact with a cooling fluid and at the other side with the gas to be condensed and/or the condensate formed in the condenser. The same applies for the wall of the redistribution chamber. In embodiments with condensation on the shell side (outside the tubes), the shell is the equipment part that contains the high pressure condensing medium and that is on the inside in contact with that medium. At outside the shell is typically exposed to ambient.

In a typical embodiment, every tube of the tube bundle has two tube ends, and for each tube one tube end is connected to an inlet redistribution chamber (for distributing fluid to a plurality of tubes) and the other tube end to an outlet redistribution chamber (for collecting fluid from a plurality of tubes).

In a preferred embodiment, the vessel comprises two tube bundles, for instance for two different cooling fluids, each tube bundle with an inlet redistribution chamber and an outlet redistribution chamber, such that the vessel contains four redistribution chambers.

The redistribution chamber comprises a wall. The wall includes a wall part with bore holes. In operation fluid flows between the redistribution chamber and the tubes connected to it through the bore holes. However, unlike a conventional tube sheet, this wall part, and more particularly the entire redistribution chamber, is spaced apart from the shell. Hence, typically no part of the redistribution chamber is in direct contact with (the internal surface of) the shell.

The redistribution chamber is connected to tube ends. In particular the wall part with bore holes is connected to tube ends, for example with crevice-free joints.

Accordingly, at least some tube ends are located inside the space enclosed by the shell (the vessel space) and are connected (for fluid flow) to an opening in the shell through a redistribution chamber and a duct extending between the redistribution chamber and the shell. The redistribution chamber is spaced apart from that shell opening, e.g. by at least 5 cm, at least 10 cm or at least 40 cm. The redistribution chamber is also spaced apart, preferably entirely, from the shell, preferably by at least 5 cm, at least 10 cm or at least 40 cm. These spacing are preferably provided by empty space that in operation can be filled with cooling fluid or condensing medium. Support elements can be present between the redistribution chamber and the shell, as well as the ducts.

Advantageously, in a preferred embodiment with cooling fluid(s) in the tubes, the high pressure is on the outside of the redistribution chamber, not on the inside.

Advantageously, the walls of the redistribution chamber can be less thick than the known tube sheets, because of the smaller dimensions of the redistribution chamber compared to a tube sheet. In particular, the redistribution chamber has a smaller surface area in cross section perpendicular to the length of the vessel compared to the shell and to a tube sheet sealing off the shell. This leads to significantly smaller forces (stresses) for which the redistribution chamber walls need to be designed.

In a preferred embodiment, a (plate) element with bore holes of the redistribution chamber (or common to a stack of redistribution chambers) has for instance only a relatively small flange around the tube bundles, such as less than 40 cm, less than 20 cm, or less than 10 cm around each tube bundle at each side, from the outer tubes of each tube bundle.

The redistribution chamber can for instance be provided with an internal load-bearing structure, such as a spacer. The walls of the redistribution chamber can be made of, or consist of, a single sheet of corrosion resistant material, such as duplex stainless steel. The weld connections of the tubes to the redistribution chamber are easier to manufacture for the preferred embodiment with a single sheet wall, especially because there is no risk of carbon steel exposure.

Furthermore, advantageously the walls of the redistribution chambers also contribute to the heat exchanging surface since in operation they can be at one side in contact with cooling fluid and at the other side with condensing medium.

The invention also pertains to a urea production plant, comprising a high pressure urea synthesis section comprising the high pressure carbamate condenser as described, a reactor and a stripper. The reactor, condenser and stripper each operate at high pressure. The stripper has a gas flow line to the condenser, the condenser has a liquid flow line to the reactor, and the reactor has a liquid flow line to the stripper for at least part of the urea solution. The reactor and condenser are optionally combined in a single vessel, which is for instance horizontally placed, and from which condensate is supplied directly to a stripper. Such a single vessel e.g. comprises a condenser part and a reactor part. Also in the case of a condenser and a reactor provided as separate vessels (typically with a vertical reactor vessel) optionally already some urea is formed in the condenser. The plant for example comprises a gas flow line from the stripper to the shell space and a liquid flow line from the stripper to the tube bundle of the carbamate condenser; or the plant for example comprises a gas flow line from the stripper to the tube bundle and a liquid flow line from the stripper to the shell space of the carbamate condenser; wherein said flow line to the tube bundle is through a duct and a redistribution chamber as described.

In operation, the urea synthesis stream from the reactor comprising urea, water, and $CO_2$ and $NH_3$ (in part as carbamate) is supplied at least in part to the stripper. Carbamate is dissociated into $CO_2$ and $NH_3$ in the stripper and a part of the unreacted components is removed from the solution as gas. In the stripper, dissociation of carbamate is promoted by heating and counter-current contact with a strip gas to promote dissociation. The stripper uses heating and for instance a supply of high pressure $CO_2$ as stripping agent, so-called thermal stripping is also possible. The heating in the stripper is typically indirect heat exchange with steam, typically with steam on the shell side and the urea synthesis stream in the tubes of a shell-and-tube heat exchanger used as stripper. Stripped urea solution, still containing some carbamate and $NH_3$, is typically expanded to a lower pressure and supplied to a recovery section wherein more carbamate is removed from the urea solution; the recovery section includes e.g. MP recovery with LP recovery section downstream in series, or only LP recovery. The mixed gas stream from the stripper containing $NH_3$ and $CO_2$ is supplied to the high pressure condenser, either to the tubes or to the shell space.

In a preferred embodiment, the mixed gas stream is supplied to the shell space, through an opening in the shell. One or more cooling fluids are supplied to the tubes, through a duct and a redistribution chamber as described (with separate ducts and redistribution chambers for different cooling fluids). Liquid condensate is formed and is in this preferred embodiment present in the shell space, with optionally gas at the top part of the shell space. The condensed liquid is in contact with the tubes such that the condensate is typically subcooled.

In this preferred embodiment, a gas distributor, such as a sparger, is used to distribute the gas to be condensed in the shell space, in particular for distribution in the length direction of the condenser. The sparger is e.g. a tube having an inlet connected to an inlet opening of the shell, optionally with arms, and having plurality of outlet openings for gas, wherein the outlet openings are spaced apart in the length direction. The arms extend in the width of the vessel and have openings for gas. A preferred carbamate condenser comprises such sparger. For horizontal condensers, both the gas distributor and the straight parts of the tubes extend in parallel in the length direction; preferably at least a part of the gas distributor is arranged below the straight parts. This advantageously provides for improved distribution of heat of condensation in the shell.

In some embodiments, ammonia is also introduced into the shell space, e.g. using a liquid distributor, especially if a $CO_2$ stripper is used.

In some embodiments, the heat of condensation is at least in part withdrawn by producing steam (water vaporization) in at least some of the tubes in case of condensation in the shell space, and in the shell space in case of condensation in the tubes, the steam is e.g. formed from process condensate.

The parts of the carbamate condenser that are in contact with process medium, especially at higher temperature (for example the process medium condensing at high pressure in the condenser) are usually made from corrosion resistant materials, in particular urea grade steel, such as an austenitic-ferritic duplex stainless steel (duplex steel). For instance the shell is at the inside typically provided with overlay welding (i.e. a weld overlay) or internal lining made of urea grade steel or other corrosion resistant metal, e.g. duplex austenitic-ferritic stainless steel, AISI 316L steel, or INOX 25/22/2 Cr/Ni/Mo steel. Such internal lining is typical for the shell of a high pressure carbamate condenser. The outside shell is e.g. a carbon steel shell and is e.g. at least 30 mm or at least 40 mm thick.

In some embodiments, the HP carbamate condenser comprises two tube bundles. This can be used to implement a process wherein two different cooling fluids are used, for instance a first tube bundle for producing steam from water, and a second tube bundle wherein an aqueous solution comprising urea and carbamate is heated to cause dissociation of carbamate.

Such a condenser can for instance be used in a plant and process as described in US 2015/0119603.

In an embodiment the HP condenser with two tube bundles is used in a urea production process wherein in a first tube bundle steam is produced from water (also referred to as condensate). In a second tube bundle a solution containing carbamate (and typically also urea) is heated by the heat of condensation received from the high pressure process medium on the shell side, such that at least part of the carbamate in the solution in the second tube bundle dissociates into $NH_3$ and $CO_2$. The solution is for instance obtained as the stripped urea solution from the HP stripper, or as a part of the urea synthesis solution from the reactor that is not stripped in the HP stripper. For example a urea solution that is a part of the liquid from the reactor (optionally, from combination vessel comprising the condenser and the reactor) and/or urea solution that is at least a part of the liquid from the stripper, is supplied to the second tube bundle, in particular through the inlet redistribution chamber and the inlet duct to the second tube bundle, optionally with intermediate steps such as expansion and gas/liquid separation (flashing). For instance, all or a part of the urea solution exiting the stripper is expanded, optionally flashed, and optionally further expanded and supplied at medium pressure (e.g. 10-35 bar) to the second tube bundle.

In some embodiments, the second tube bundle receives a carbamate containing solution, for instance in urea production processes involving supplying a urea solution to the second tube bundle directly or indirectly from the reactor (or reactor part), e.g. from the reactor, the stripper, or from a recovery section, preferably through an inlet duct and inlet redistribution chamber. In such embodiments thermal dissociation of carbamate (to $CO_2$ and $NH_3$ gas) can take place in the second tube bundle.

The high pressure condenser can for instance be used in a urea production process of the stripping type, wherein a part of the urea solution from the reactor is sent to a high pressure stripper, and another part of the solution bypasses the stripper and is sent to a medium pressure treatment step involving dissociation of carbamate by heating the solution at medium pressure. The invention also pertains to such a process. An example of such a process, using a different type high pressure condenser, is described US 2004/0116743. In the operation of the high pressure carbamate condenser of the present invention, and in a preferred process of the invention, the medium pressure treatment step is for instance carried out by passing the urea solution through the (second) tube bundle of the high pressure carbamate condenser in indirect heat exchanging contact with condensing gases in the condenser that are received from the stripper. In a further embodiment, the carbamate condenser is used for raising steam (e.g. in a tube bundle), which steam is used for supplying heat to a medium pressure dissociation step of urea solution obtained from the stripper or non-stripped urea solution from the reactor.

For conventional HP carbamate condensers, a challenge in case of having in operation carbamate containing liquid(s) in at least some of the tubes as well as in the shell space is the risk of corrosion, and the manner of tube to tube sheet connection, e.g. for the pool condenser with a tube sheet as illustrated in US 2015/0119603. The present invention provides the important advantage that the redistribution chamber, in particular the wall part with bore holes, that is on both sides exposed to corrosive carbamate-containing solution, can in an embodiment be made of (and consist of) single sheet corrosion resistant steel, such as single sheet duplex stainless steel. This is in particular the case when the condensation is on the shell side. Multi-layered walls of the chamber are also possible, especially if all layers are of corrosion-resistant material. In some embodiments, the thickness of the wall part with bore holes for the tubes is 0.5-2 times the thickness of any other part of the wall of the redistribution chamber, the wall part with bore holes being a flat plate. For instance, if the other parts of the redistribution chamber have walls of 1-2 cm thickness, the wall part with the bore holes for the tubes has a thickness of 0.5-4 cm. In some embodiments, the thickness of the wall part with bore holes for the tubes is 0.9-1.1 times the thickness of the other parts of the wall of the redistribution chamber. An advantage of the invention is that the wall part with the bore holes for tubes does not need to be a very thick plate such as in the case of a tube-sheet.

In an example embodiment, the condenser comprises two U-shaped tube bundles arranged with, in vertical direction, ABBA, wherein A is a straight part of the first tube bundle and B is a straight part of the second tube bundle, or wherein A is a straight part of the second tube bundle (in operation used e.g. for carbamate dissociation) and B is a straight part of the first tube bundle (in operation used e.g. for raising steam), and preferably with a vertical stack of four redistribution chambers connected to the two tube bundles. In such embodiment, the bends of the U-shaped tube bundle can be arranged in concentric fashion (in particular in cross-section in the length-height plane). Alternatively, the arrangement can be AABB which would give e.g. two sets of bends, within each tube bundle concentric and the two sets arranged above each other.

In a preferred embodiment of the urea production plant of the invention, the high pressure carbamate condenser comprises a tube bundle that is connected through a redistribution chamber and a duct to a feed line. The feed line is used for feeding urea solution that also contains carbamate to the tubes of the tube bundle. The feed line is connected to the stripper for receiving stripped urea solution from the stripper and/or is connected to the reactor for receiving a part of the urea solution from the reactor. In a preferred embodiment, the feed line comprises an expansion device and preferably a gas/liquid separator for separating gas from the expanded urea solution. Preferably the feed line is configured for supplying at least a part of the expanded urea solution to the duct.

In a preferred embodiment, the tube bundle (receiving urea solution also comprising carbamate) is connected through an outlet redistribution chamber and a duct to a gas/liquid separator. The gas/liquid separator preferably has a liquid flow connection to a recovery section and a gas flow connection to a second condenser. The ammonia and $CO_2$ obtained by thermal dissociation of carbamate in the tubes, is condensed at least partially in the second condenser. Preferably the second condenser operates at medium pressure. Preferably the condensation is carried out in heat exchanging contact with an evaporation section of the urea plant, such that the heat of condensation is used for evaporation of water from a urea solution. Preferably the second condenser has a liquid flow connection for a carbamate recycle stream to the high pressure carbamate condenser, and more preferably to the shell space.

The HP condenser may in addition comprise a second tube bundle connected to a feed line for process condensate (i.e. water) and connected to a drain line for steam.

In a preferred embodiment, the condenser comprises one or more pairs of the ducts, each pair including an inlet duct and an outlet duct. The condenser preferably comprises one or more pairs of the redistribution chambers, each pair including an inlet redistribution chamber for distributing cooling fluid feed from the inlet duct to a plurality of tubes and an outlet redistribution chamber for combining heated cooling fluid from a plurality of tubes to the outlet duct. For each pair the redistribution chambers are typically arranged at the same side of the straight tube parts, in case of a U-shaped tube bundle, or at opposed sides (in length direction) of the tubes in case of straight tube bundle.

In a preferred embodiment, the redistribution chamber comprises a plurality of elements (such as plate elements) and is hence not completely unitary. These elements together provide the wall of the redistribution chamber. At least one of the elements is provided with bore holes for the tube, and the same or another element (e.g. other plate) is provided with a hole for a duct. Preferably, at least one other element is openable and closable, e.g. removable, thereby providing access to the inside of the redistribution chamber. The element is for instance a cover plate. This element can be used for making the inside of the redistribution chamber accessible, e.g. for humans and/or for devices. In this way the inside of the redistribution chamber, i.e. the space for receiving the fluid, is accessible for maintenance and inspection of the redistribution chamber inside and the tubes, in particular for inspection of the tubes insides and for plugging of tubes. The plugging of tubes can involve placing a plug in a tube at a tube end connected to a redistribution chamber. In a preferred embodiment, the redistribution chamber comprises fasteners for fastening the openable element to at least one other element, such as bolts. For instance, a box shaped redistribution chamber having an openable front plate may comprise a front plate having openings and side plates with recesses (e.g. a threaded hole) aligned with the openings. The openings and recesses can receive a fastener such as a bolt.

The redistribution chamber may furthermore comprise spacers for spacing wall parts (e.g. plate elements) from each other, e.g. to provide resistance against compression forces.

The vessel preferably comprises supports for the redistribution chamber, for instance arranged below the redistribution chamber and on the shell. For example support elements can be provided below (and e.g. at the same position in the length direction of the vessel as) the wall part provided with bore holes. The support may comprise a recess for receiving a lug of a redistribution chamber for locking the redistribution chamber in place. The redistribution chamber or e.g. a stack of redistribution chambers are e.g. provided with fixation means for holding the chambers in place in the shell.

Preferably, the surface area of the transversal cross-section of a redistribution chamber (cross section perpendicular to the length axis of the vessel) is less than 90% or less than 80% or less than 40% of the surface area of the cross-section of the vessel (in particular, of the surface area enclosed by the shell in that cross-section).

In case of a (vertical) stack of redistribution chambers, the surface area of the cross-section of the stack in the width-height plane (perpendicular to the central length axis of the vessel) is e.g. less than 90% or less than 80% or less than 70% of the surface area of the cross-section of the vessel (in particular, of the surface area enclosed by the shell in that cross-section).

Preferably, the shell space is a single undivided space wherein all parts of the space are in fluid communication with each other; also in such embodiments the shell space can include baffles to divide the shell space in compartments which are not completely sealed off from each other. Preferably the shell is in contact with the shell space, and preferably the entire inner surface of the shell is in contact with the shell space. Preferably each duct extends through the shell space. Preferably each duct comprises a length segment wherein the entire outside wall of the duct is exposed to the shell space. Preferably the front plate of a (or each) box shaped redistribution chamber (with holes for connecting with tubes in an opposite back plate) is on the outside side exposed to the shell space.

In some embodiments, at least one redistribution chamber is in operation at least partly submerged in condensed liquid, preferably each redistribution chamber is at least partially submerged in condensed liquid and preferably at least one redistribution chamber is entirely submerged in condensed liquid, wherein the condensed liquid is condensed in the shell space.

In a preferred embodiment, the shell comprises an essentially cylindrical middle part and two cap parts. Each cap part may comprise a plurality of shell parts. A cap part is for instance a substantially hemispherical part, optionally with a manhole and plate. The two cap parts close the middle part at opposed ends, in particular at opposed ends in the length direction. Preferably the shell space is a single shell space defined by the middle part and cap parts. Preferably the shell space is not divided, e.g. by dividing walls; yet can include baffles. Preferably fluid can flow from the gas distributor to both of the cap parts.

High pressure carbamate condensers are different from other types of heat exchangers, in particular hot gas coolers, by a number of features, which are preferred for the inventive carbamate condenser. A horizontal carbamate condenser configured for condensation in the shell may for instance include baffles (or partitions), which divide the shell space in compartments in the length direction and which extend from the bottom of the vessel, but not entirely to the top thereby leave a gas discharge area at the top of the shell; the top of the baffles define the liquid level of the condensate in operation. Some of the baffles can have openings e.g. at the vertical height of the tube bundle. Typically, the most downstream baffle has no opening in it, such that liquid condensate flows over the baffle top to the liquid outlet in the shell. Hence, the shell section comprises a weir. This allows for control of the level of the condensate in the condenser, especially to completely submerge the tube bundle. Furthermore typically the tube bundle, especially U-shaped tube bundle, has a once-through configuration or each cooling fluid (urea solution and/or process condensate).

A carbamate condenser with condensation in the tubes, e.g. of the horizontal kettle type, comprises for example an ejector at the inlet of the carbamate solution, and for instance comprises a mixing zone for inlet of gas to be condensed and carbamate solution. The carbamate condenser has for instance a conduit for recycle carbamate solution from an outlet end of a tube to an inlet for gas to be condensed.

In case of a vertical carbamate condenser which is configured for condensation in the shell space, the condenser comprises for instance a packed part at the top, e.g. a part with a packing for scrubbing off-gas with a solution supplied through an inlet of the shell above the packed part, in particular an inlet for carbamate solution, and a down pipe arranged below the packed part but above the U-bend of the tube bundle to a part of the condenser below said bend. The vertical carbamate condenser preferably has an outlet for liquid of the shell, optionally with a down pipe, such that in operation a liquid level is maintained above the U-bend of the tube bundles, wherein tube ends are at the bottom of the vessel.

The ducts preferably comprise, or are made of, a corrosion resistant steel, such as a duplex stainless steel. For instance the ducts are made entirely of such steel. The wall parts of the redistribution chambers, and any internal structures such as spacers that are in operation in contact with carbamate, are preferably made of corrosion resistant steel, such as duplex stainless steel. The tubes, and the preferred internal lining of the shell, are preferably made of corrosion resistant steel, such as duplex stainless steel.

Suitable duplex stainless steel for said parts of the carbamate condenser include for example the steel available as Safurex® steel and having composition 29Cr-6.5Ni-2Mo—N, which is also designated by ASME Code 2295-3 and by UNS S32906, or e.g. steel available as DP28W™ steel and having composition 27Cr-7.6Ni-1 Mo-2.3W—N, which is also designated by ASME Code 2496-1 and by UNS S32808. Safurex® steel has for instance the composition (% by mass): C: max. 0.05, Si: max. 0.8, Mn: 0.3-4.0, Cr: 28-35, Ni: 3-10, Mo: 1.0-4.0, N: 0.2-0.6, Cu: max. 1.0 W: max. 2.0 S: max. 0.01 Ce: 0-0.2, balance Fe and (unavoidable) impurities. Preferably the ferrite content is 30-70% by volume and more preferably 30-55%. More preferably, the steel contains (% by weight): C max. 0.02, max. 0.5 Si, Cr 29 to 33, Mo 1.0 to 2.0, N 0.36 to 0.55, Mn 0.3 to 1.0, balance Fe and impurities. Also suitable is a duplex stainless steel having the composition weight % (wt %): C max 0.030; Si max 0.8; Mn max 2.0; Cr 29.0 to 31.0; Ni 5.0 to 9.0; Mo less than 4.0; W less than 4.0; N 0.25-0.45; Cu max 2.0; S max 0.02; P max 0.03; balance Fe and unavoidable occurring impurities; and wherein the content of Mo+W is greater than 3.0 but less than 5.0 (wt. %), furthermore preferably with a steel composition as described in WO 2017/014632 hereby incorporated by reference. In some embodiments the shell comprises an internal lining made of such steels.

Each duct has a first duct end connected with a wall of the redistribution chamber and a second end connected with the shell. The first duct end is aligned with an opening in the wall and the second duct end is aligned with an opening in the shell, such that fluid can flow from outside the shell to the redistribution chamber through the duct. The duct is at least in part located in the vessel. The first duct end is located in the vessel. The duct extends through the vessel space. Furthermore, the outer surface of the duct is exposed to the shell space.

The duct may consist of one or more duct parts, e.g. duct parts arranged in series and connected with each other.

The first duct end is connected to a redistribution chamber, e.g. with a weld. The first duct end is for example placed radially outwardly of the tube ends connected to that redistribution chamber, i.e. further removed from the central length axis of the vessel in a direction perpendicular to the length. In an example embodiment with a box-shaped redistribution chamber with a bottom, top, front, back and two side plates, the duct end is for instance attached to a side, top or bottom plate, and the tube ends are attached to the back plate and the front plate is e.g. a cover plate that can be opened for maintenance and inspection. In principle, the duct can also be connected to the back plate or to the front plate. In an example embodiment with a box shaped redistribution chamber, a duct is connected to the front plate and a side plate can be opened.

In a preferred embodiment a plurality of redistribution chambers are stacked on each other, to give a stack, preferably of box-shaped redistribution chambers and preferably a vertical stack. Preferably a plate element is common to the stacked redistribution chambers, preferably a plate element with bore holes.

Preferably the tube bundle contains U-shaped tubes wherein each tube has a bend and two legs. Preferably the stack of redistribution chambers includes an inlet redistribution chamber and an outlet redistribution chamber connected to the same U-shaped tube bundle.

In case of a (vertical) stack of preferably box-shaped redistribution chambers, various plates can be common to the redistribution chambers of the stack, this can be the case e.g. for a back plate (e.g. with bore holes for connecting with a tube bundle) and for a side plate. A horizontal plate can be common to two adjacent chambers, providing a top plate and a bottom plate, in particular when the chambers receiving fluid at the same pressure in operation. In case of a vertical stack of four or more redistribution chambers, for the top redistribution chamber a duct can be connected to a top plate, for a bottom redistribution chamber a duct can be connected to a bottom plate, and for the redistribution chambers in the middle ducts can be connected to a side plate. In a preferred embodiment, a redistribution chamber is provided with ducts at two opposed side plates, and these are in operation for example used both as inlet or both as outlet. This may advantageously contribute to good distribution of fluid over the tubes and efficient removal of fluid from the tubes. In particular because in some embodiments a box shaped redistribution chamber has a width (from side to side) that is longer than the height of the redistribution chamber, and wherein the same applies for the area of the back plate that is provided with holes.

In an example embodiment with a stack of redistribution chambers, all ducts connected to that stack extend to the top of the shell. In combination with e.g. support structures for the tube bundle in the vessel between the shell bottom and the tube bundle, this may allow for adapting to expansion and/or contraction of the equipment. In case of a stack of redistribution chambers, the chambers may have e.g. a common shared back plate, and for a vertical stack also common shared side plates.

In some example embodiments, the spacing in the length direction between a first and second end of a duct is for one or more ducts (or even for all ducts) less than 20% or less than 10% of the length of the vessel, or less than 20% or less than 10% of the length of the straight parts of the tubes.

In a further embodiment, one or more ducts extend in the length direction, for example with the ducts arranged substantially parallel (e.g. less than 5° deviation) with the (straight parts) of the tubes. In some example embodiments, the spacing in the length direction between a first and second end of a duct is for one or more or even all ducts, more than 10% or more than 20% of the length of the straight parts of the tubes.

Generally, for a redistribution chamber, the number of tubes connected to that redistribution chamber is at least 10 times higher than the number of ducts connected to that redistribution chamber, e.g. at least 50 times or at least 100 times higher. Accordingly, the ducts generally have a surface area in transversal cross section (perpendicular to the flow direction) of the internal flow space of the duct that is at least 10 or at least 20 times larger than that of a tube.

Each duct has at least two duct ends, wherein duct ends refers to end parts and not only to the side edge. A duct may also have e.g. three duct ends in case of a Y-shaped duct. A duct ends is connected to the redistribution chamber. For instance, a duct edge may be adjoined to a (planar) side of a redistribution chamber wall with a crevice-free joint. A duct end may also be inserted through an opening in a redistribution chamber wall, for instance with the crevice between the wall and duct part being sealed off by a weld.

In the same way, a duct end (end part) is connected with the shell, e.g. a duct end may be adjoined to the shell, for instance with a crevice free joint. In case the shell wall includes a carbon steel element and the fluid to be transported through the duct includes carbamate, the duct end or a part of the duct can be inserted through an opening in the shell. A crevice between the inserted duct part and the hole surface of the shell (including any exposed carbon steel) can be closed off by welding also at the inner side of the shell as the well place will be accessible. Optionally, a duct part such as a sleeve (e.g. of duplex stainless steel) is first inserted through a hole, the crevice is sealed off e.g. by welding, and the inserted duct part (e.g. sleeve) is connected to another duct part e.g. by internal bore welding. For instance the condenser comprises a duct end part inserted through an opening in the shell and having a sealed crevice between the inserted duct part and the shell.

In an embodiment wherein a redistribution chamber is provided with a plurality of ducts, these ducts are optionally connected to a header (or joint segment) which can be placed inside or outside the vessel. In some embodiments, the duct comprises a joint segment (e.g. T-joint) which connects at least three duct segments. With such a duct, two duct ends can e.g. be connected to the redistribution chamber and one duct end to the shell. In an example embodiment, an inlet duct is connected to a bottom plate of a bottom redistribution chamber of a vertical stack of redistribution chambers by two or more duct segments each connected to the bottom plate, at least one duct segment connected to the shell, and a joint segment located inside the vessel space joining the duct segments. The at least two duct segments connected to the redistribution chamber can be spaced apart from each other for optimally distributing fluids over the tubes.

The condenser can be constructed for example with a method comprising mounting a tube bundle in the shell (having at least one open end), such as on support baffles. The invention also pertains to such a construction method. The method can comprise connecting the redistribution chambers to the tube ends before or after mounting the tube bundle, e.g. using internal bore welds. For instance a tube bundle connected to a stack of redistribution chambers is mounted in the shell. The method may involve connecting the ducts to the redistribution chamber after mounting the tube bundle. The ducts can be inserted through the shell before or after the mounting. The method may involve closing the vessel by e.g. joining a closing cap (e.g. a hemi-head) to an essentially cylindrical middle part of the vessel having at least one open end, e.g. at the middle part end where the redistribution chamber is located.

Example embodiments of the invention are illustrated and discussed in connection with the drawings, these drawings do not limit the invention or the claims.

FIG. 1 shows a reference high pressure carbamate condenser not according to the invention. The condenser (100) is provided as a shell-and-tube heat exchanger (101) and is configured as a horizontal submerged condenser with a U-shaped tube bundle (103) for cooling fluid and having in operation the gas to be condensed in the shell space (105). A part of the bottom half of the condenser (100) is shown in FIG. 1. The heat exchanger (101) comprises a vessel (102), the vessel comprises a shell (1) and a tube bundle (103). The shell is designed to withstand high pressure and encloses a vessel space (104). The vessel (102) also comprises a header (107). The header (107) is not enclosed by the shell (1) and is outside the vessel space (104). The tubes (2) of the tube bundle (103) are provided in the vessel space (104). The space between the tubes (2) and the shell (1) is the shell space (105) for receiving gas to be condensed. Accordingly, the vessel comprises a gas inlet (4) to the shell space (105), and an outlet (5) for liquid from the shell space (104), and respective openings for process medium in the shell (1). The vessel furthermore comprises a carbamate recycle inlet (13) comprising an opening in the shell (1). The vessel further contains a gas distributor (6) that is connected to the gas inlet (4). The gas distributor (6) is configured for distributing the gas to be condensed (e.g. mixed gas from a high pressure stripper of a urea plant) in the shell space (105).

The vessel (102) further comprises a tube sheet (108). The tube sheet separates the shell space (105) from the header (107) and therefore needs to withstand large pressure differences. One open end of the essentially cylindrical shell (1) is sealed off by the tube sheet (108). The tube sheet contains bore holes (110) for cooling fluid. The ends (3) of the tubes (2) are connected to the tube sheet (108), such that fluid can flow between the tubes and the header (107). The header is provided with an opening (109) that is used as inlet or outlet, such that cooling fluid flows between the opening (109) to a large number of tubes (2), e.g. more than 100 tubes. The tube sheet (108) is for instance an essentially circular metal plate and is typically a thick carbon steel plate (e.g. about 30 to 60 cm carbon steel) lined with corrosion resistant steel on the side exposed to the shell space (105), such as with a duplex stainless steel alloy lining (which includes e.g. a weld overlay).

For the reference carbamate condenser of FIG. 1 (not according to the invention), the construction of the tube sheet (108) is challenging and expensive, in view of the need to withstand high pressure, the exposure of at least one side to the very corrosive process medium, and the very large number of tubes. Furthermore any crevices between the tubes and tube sheet introduce a high risk of crevice corrosion because they are in contact with carbamate containing medium. Crevices are present for instance in case of tube legs extending through the bore holes, e.g. with a bore diameters (slightly) larger than the outer diameter of the tube. Crevice corrosion is particularly severe for metal parts in contact with carbamate. Crevice corrosion can refer to the difficulty of maintaining a passivation layer on the steel with passivation agents (such as oxygen) in crevices due to the restricted flow in crevices. Corrosion also occurs in crevices if carbon steel is exposed in such crevices. Therefore in known pool condensers the tubes are frequently not inserted into the bores, but are joined to the tube sheet in a crevice free manner using e.g. internal bore welding. The exposure of the carbon steel part of the tube sheet to process condensate and steam in the bores is not problematic.

In case that a urea solution which also contains carbamate is provided as cooling fluid into header (107), such as when used for a process as described in US 2015/0119603, a corrosion protective layer is also necessary on the side of tube sheet (108) exposed to the header (107), and the carbon steel surface of the bore holes (110) should not be exposed to the cooling fluid. The alternative of a single sheet duplex stainless steel alloy tube sheet is not practically feasible, because homogenous duplex stainless steel plates having a thickness (e.g. 30 to 60 cm) sufficient to contain the high pressure medium are not feasible to manufacture, at least in a practically acceptable way.

In US 2015/0086440 a construction method is described wherein sleeves are inserted in bore holes through the tube sheet such that the sleeves extend through the tube sheet. The sleeves are much shorter than the tubes. The sleeves can be (externally) welded on both sides of the tube sheet, such that the carbon steel layer of the tube shield is sealed off from the fluid in the shell space (105) and from fluid in the header (107). At one side of the tube sheet, the sleeves are subsequently connected with the legs of the U-shaped tube bundle with an internal bore weld. Hence, after welding the sleeves to the tube sheet, the tube ends are connected to the sleeves by welding from the inside by inserting the welding probe in the sleeves from the low pressure side (header side) and forming an internal bore weld.

Accordingly, the external welding of the sleeves to the tube sheet is carried out prior to connection of the sleeves to the tube bundle, because otherwise the tube bundle (with a large number of closely spaced tubes) prevents access at one side of the tube sheet. However, a disadvantage is that for each tube three welds are necessary, causing high construction costs.

If in the method of US 2015/0086440 the sleeve would be omitted and the tubes were directly connected to the tube sheet with internal bore welding, the carbon steel plate inside the tube sheet would exposed at the bore holes to the carbamate present in the urea solution used as cooling fluid inside the tubes. This would induce corrosion. If the tubes were inserted into the bore holes, a crevice would be present between the tube ends inserted in the bore holes and the tube sheet, i.e. a gap between the outside of the tube and the inside of the tube-sheet hole, allowing process medium to contact the carbon steel part of the tube sheet. In the present invention the wall of the redistribution chamber (including the wall part with bore holes as in a conventional tube sheet) can advantageously be made of single sheet duplex stainless steel, such that an urea solution containing carbamate which is used as cooling fluid can be contacted with the surface of the bore holes without inducing excessive risk of corrosion.

In order to have a longer residence time of the condensate in the shell space in the condenser of FIG. 1, one option is increasing the diameter of the shell, such that the shell has much larger surface area in cross section than the tube bundle, e.g. as illustrated in U.S. Pat. No. 5,767,313. A disadvantage is that the diameter of the tube sheet also increases, because the tube sheet is used for sealing off one end of the shell, and hence the stress induced by the pressure differences also increases.

Figure 2A:
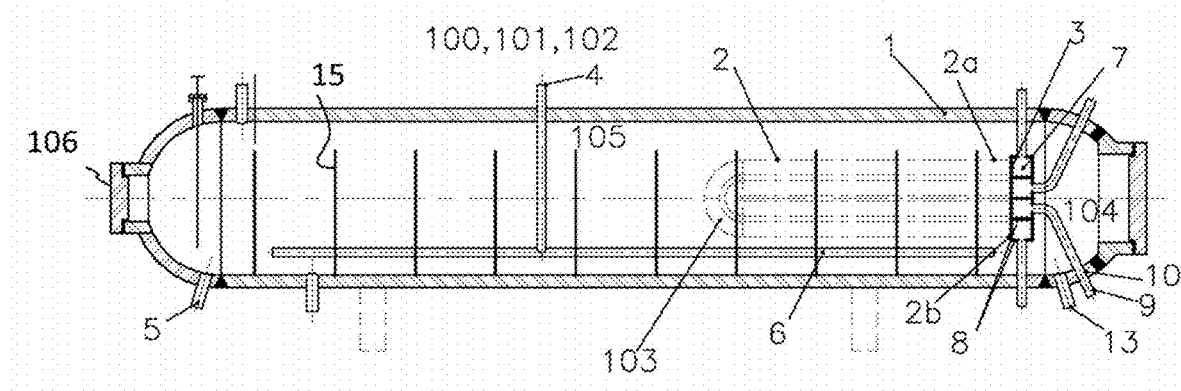
FIGS. 2A-2D illustrate examples of a high pressure carbamate condenser.
Figure 2B:
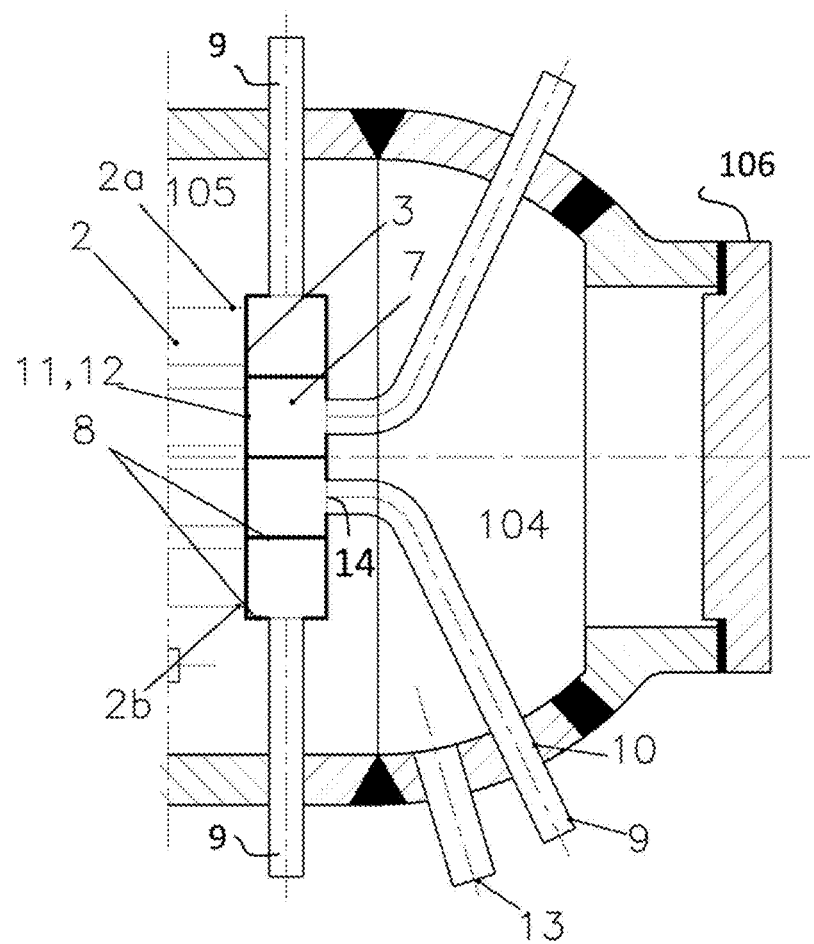
Figure 2C:
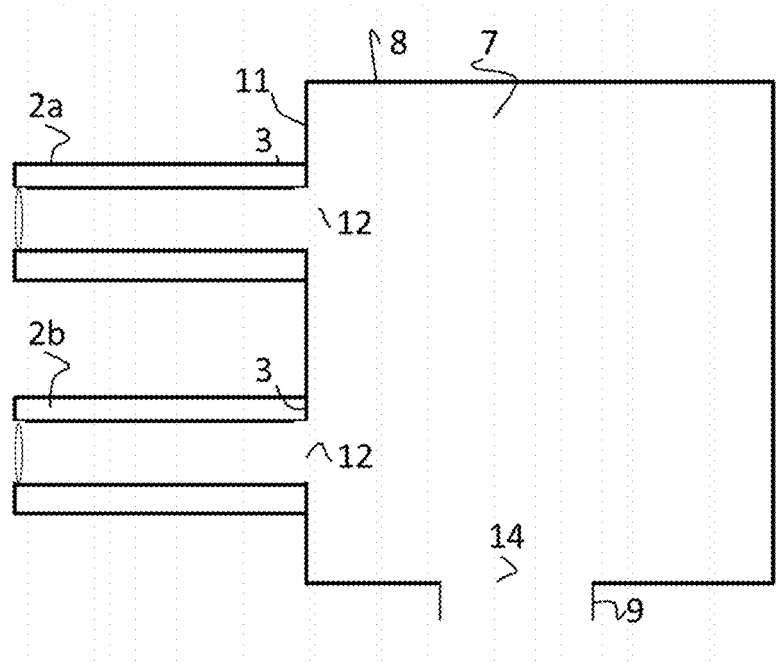

FIG. 2A illustrates an example of a carbamate condenser (100) according to the invention. FIG. 2B shows an enlarged part. Instead of a header (107) and a tube sheet (108) as in FIG. 1, the carbamate condenser (100) contains a redistribution chamber (7) with a wall (8). The wall (8) is configured for separating fluid in the redistribution chamber (7) from fluid in the shell space (105). These two fluids generally have a different composition in operation. The redistribution chamber (7) is provided inside the vessel space (104) and is therefore enclosed by the shell (1). The shell (1) is configured for holding fluid that is in fluid contact with the outer surface of the tubes (2). A plurality of tubes (2a, 2b) are connected to each single redistribution chamber (7), such that fluid can flow between the tubes (2) and the redistribution chamber (7), through openings (12) (e.g. bore holes) in the wall (8) that are provided in a part (11) of the wall (8). The ends (3) of the tubes (2) are attached to the wall (8) such that an openings of the tube end is aligned with an opening (12) of the wall (8). This is schematically illustrated in FIG. 2C, with the diameter of the tubes (2a, 2b) enlarged compared to the redistribution chamber (7). The attachment of the tube end (3) is e.g. with an internal bore weld. The redistribution chamber (7) is connected to an opening (10) in the shell (1) for (cooling) fluid by a duct (9). The duct (9) is placed in the vessel space (104) and is preferably exposed to the shell space (105). The duct (9) extends between the opening (10) of the shell (1) and the redistribution chamber (7), more in particular to an opening (14) of the redistribution chamber (7). In this way, cooling fluid can be transported between the opening (10) in the shell (1) and the tubes (2) through the redistribution chamber (7) and the duct (9) while the cooling fluid is separated from process medium fluid in the shell space (105). In operation, the duct (9) is on the inside in contact with cooling fluid and on the outside in contact with process medium in the shell space (105). As illustrated in FIGS. 2A and 2B, the carbamate condenser (100) also contains a manhole (106) and baffles (15).

Figure 2D:
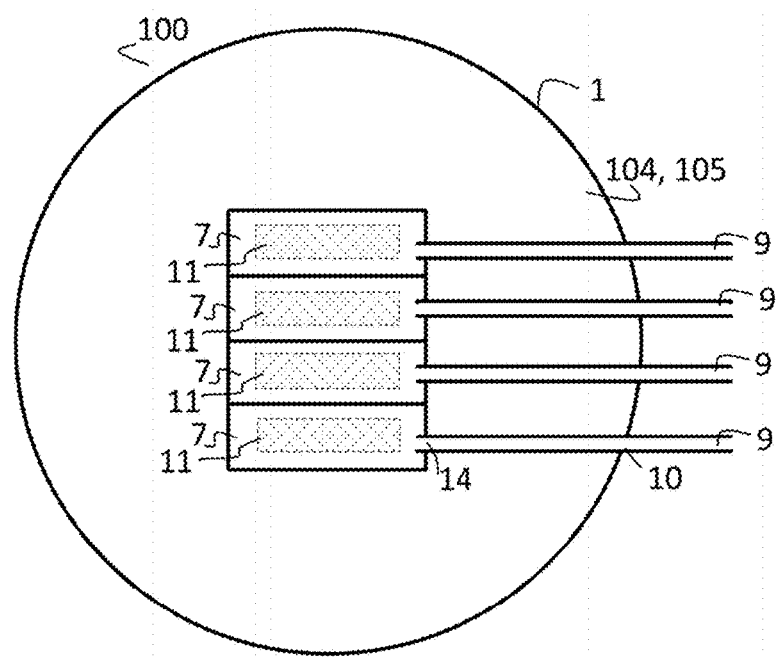

FIG. 2D schematically illustrates a cross section view perpendicular to the length of an example embodiment. The carbamate condenser (100) comprises vertical stack of 4 box-shaped redistribution chambers (7) each having a duct (9), the part (11) with bore holes is indicated in each redistribution chamber (7). The arrangement of the ducts (9) in FIG. 2D is schematic, numerous variations are possible. The ducts (9) generally extend from the redistribution chambers outwardly to an opening (1) in the shell (1). Reference numbers which are the same for FIGS. 1 and 2 preferably have the same features in FIG. 2 as described in connection with FIG. 1.

Figure 3:
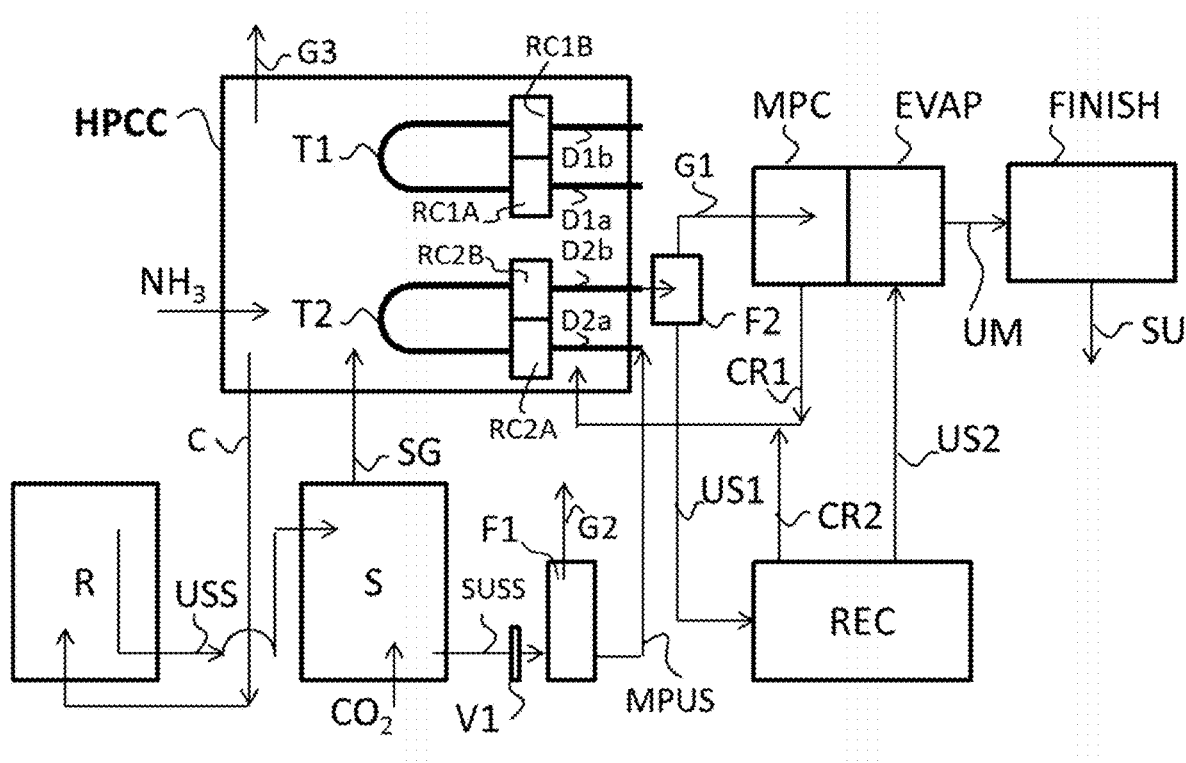
FIG. 3 schematically illustrates an example of a urea plant.

FIG. 3 illustrates an example urea plant according to the invention. The plant comprises a high pressure synthesis section comprising a urea reactor R, a stripper S, and a HP carbamate condenser HPCC. The reactor R has a liquid flow connection for urea synthesis solution USS to the stripper S which uses $CO_2$ feed for stripping, in addition to heating by indirect heat exchange with steam. Optionally, reactor R is combined with the condenser HPCC in a single vessel having a liquid flow connection to the stripper S. The urea synthesis solution USS also contains carbamate, ammonia and water, which are to be removed (at least in part) from the final urea product using the stripper S and a recovery section REC comprising a low pressure section and e.g. consisting of a low pressure section without medium pressure section. Downstream of REC optionally an evaporation section EVAP is provided for water removal to give a urea melt UM that is optionally solidified in a finishing section FINISH to give solid urea product SU. The stripper S has a gas connection for mixed gas SG to the condenser HPCC. The condenser HPCC comprises two U-shaped tube bundles T1 and T2. Each tube bundle (T1, T2) comprises numerous tubes (e.g. more than 100 tubes). Each tube is connected with one end to a inlet redistribution chamber RC1A, RC2A and with the other end to an outlet redistribution chamber RC1B, RC2B. The inlet redistribution chamber (RC1A, RC2A) is connected to an inlet duct D1a, D2a. The outlet redistribution chamber (RC1B, RC2B) is connected to an outlet duct (D1b, D2b).

Condensation is carried out on the shell side of HPCC, to which also the $NH_3$ feed is supplied. The stripper S has a liquid flow connection for stripped urea solution SUSS through an expansion device (e.g. expansion valve) V1 to a flash vessel F1 for gas/liquid separation. Flash vessel F1 has a liquid connection for medium pressure urea solution MPUS which still contains carbamate to tube bundle T2. In tube bundle T2, the MPUS solution is heated and carbamate in MPUS accordingly decomposes. From the outlet of tube bundle T2, the MPUS solution is sent to a gas/liquid separator, e.g. a flash vessel (F2). The gas G1 is sent to a condenser MPC typically operating at medium pressure (MP) and in heat exchange e.g. with the evaporation section EVAP. The liquid US1 from separator F2 is sent to e.g. a low pressure recovery section (REC) for further removal of carbamate and water, and then as urea solution US2 to the evaporation section EVAP. In the recovery section REC, the urea solution is subjected to dissociation of carbamate by heating typically at low pressure, the removed gases are condensed into liquid carbamate recycle stream CR2. The condenser MPC may also receive the gas G2 from flash vessel F1, and non-condensed gases G3 from HPCC and (not shown) off-gas from R. The condensate from MPC is sent using a pump (not shown) as liquid carbamate recycle CR1 to the synthesis section, in particular to the shell space of the HPCC condenser, usually combined with a liquid carbamate recycle (CR2) from a recovery section REC. The condenser HPCC has a liquid flow connection for condensate C to the reactor. Alternatively or in addition, a part of USS can be sent from R to tube bundle T2, e.g. to F, bypassing the stripper S. In tube bundle T1 water (typically condensate) is transformed into steam (not shown).

As used herein "a" and "an" includes one or more. The term "comprising" allows for the presence of other elements than those recited. Various illustrative embodiments have been described above, in part with reference to the accompanying drawings, but the invention is not limited to these embodiments. Features of the separately described embodiments can generally be combined with each other as will be clear for the skilled person. Steps of the production processes can be implemented with corresponding units and fluid flow connections of the inventive plant. The process of the invention preferably is carried out in a plant as described and using the high pressure carbamate condenser as described with all preferred device features applying equally for the process. Reference signs in the claims to the drawings provide example illustrations only and do not limit the claims.

The invention claimed is:

1. A shell-and-tube heat exchanger which comprises a vessel which comprises a shell and at least one tube bundle, wherein the shell encloses a vessel space, wherein the tube bundle comprises tubes having ends, and wherein a shell space is provided between the tubes and the shell,
    wherein the heat exchanger further comprises a redistribution chamber located in said vessel space, wherein said redistribution chamber comprises a wall for separating a first fluid in the shell space from a second fluid inside the redistribution chamber, wherein the wall of the redistribution chamber comprises a flat plate comprising a plurality of bore holes,
    wherein a plurality of said tubes are connected to a single redistribution chamber at said bore holes such that said second fluid can flow between said tubes and said redistribution chamber,
    wherein the heat exchanger further comprises a duct extending from an opening for the second fluid in said shell through said vessel space to said redistribution chamber such that the second fluid can flow between a tube end and said opening for the second fluid in said shell through said redistribution chamber and said duct.

2. The heat exchanger according to claim 1, wherein the duct has a first duct end connected with a wall of the redistribution chamber and a second end connected with the shell.

3. The heat exchanger according to claim 2, wherein the first duct end is aligned with an opening in the wall and the second duct end is aligned with an opening in the shell, such that fluid can flow from outside the shell to the redistribution chamber through the duct; wherein the duct is at least in part located in the vessel; wherein the first duct end is located in the vessel; wherein the duct extends through the vessel space; and wherein the outer surface of the duct is exposed to the shell space.

4. The heat exchanger according to claim 2, wherein the first duct end is connected to said redistribution chamber.

5. The heat exchanger according to claim 4, wherein the first duct end is connected to said redistribution chamber with a weld.

6. The heat exchanger according to claim 4, wherein the first duct end is placed radially outwardly of the tube ends connected to that redistribution chamber.

7. The heat exchanger according to claim 1, wherein the duct has an outer surface exposed to the shell space.

8. The heat exchanger according to claim 1 configured for condensation of a compound.

9. The heat exchanger according to claim 8, wherein the compound is carbamate.

10. The heat exchanger according to claim 1 configured for operation at pressures below 100 bar.

11. The heat exchanger according to claim 1, wherein the flat plate has a thickness that is 0.5 to 2 times the thickness of any other part of the wall of the redistribution chamber.

12. The heat exchanger according to claim 1, wherein the redistribution chamber comprises an internal load bearing structure.

13. The heat exchanger according to claim 1, wherein the internal load bearing structure is a spacer.

* * * * *